(12) United States Patent
Malave et al.

(10) Patent No.: US 12,115,349 B2
(45) Date of Patent: Oct. 15, 2024

(54) SYSTEMS AND METHODS FOR MANAGING DIABETES

(71) Applicants: Luis Malave, San Marcos, CA (US); Jesse Jaejin Kim, San Jose, CA (US); Yong Ho Jeon, Gyeonggi-do (KR); Dong Min Lee, Gyeonggi-do (KR)

(72) Inventors: Luis Malave, San Marcos, CA (US); Jesse Jaejin Kim, San Jose, CA (US); Yong Ho Jeon, Gyeonggi-do (KR); Dong Min Lee, Gyeonggi-do (KR)

(73) Assignee: EOFLOW CO., LTD. (KR)

( * ) Notice: Subject to any disclaimer, the term of this patent is extended or adjusted under 35 U.S.C. 154(b) by 927 days.

(21) Appl. No.: 17/166,372

(22) Filed: Feb. 3, 2021

(65) Prior Publication Data
US 2021/0213196 A1    Jul. 15, 2021

Related U.S. Application Data

(63) Continuation-in-part of application No. 15/943,702, filed on Apr. 3, 2018, now Pat. No. 11,007,319.

(51) Int. Cl.
*A61M 5/168* (2006.01)
*A61M 5/172* (2006.01)
*G16H 20/17* (2018.01)

(52) U.S. Cl.
CPC ........ *A61M 5/1684* (2013.01); *A61M 5/1723* (2013.01); *G16H 20/17* (2018.01)

(58) Field of Classification Search
CPC ............. A61M 5/1684; A61M 5/1723; A61M 2205/18; A61M 2205/3553;
(Continued)

(56) References Cited

U.S. PATENT DOCUMENTS

| 2006/0187003 A1* | 8/2006 | Terenna | G04G 11/00 368/244 |
| 2011/0071482 A1* | 3/2011 | Selevan | G04F 3/08 604/304 |

(Continued)

FOREIGN PATENT DOCUMENTS

| WO | WO-9630078 A1 * | 10/1996 | ............. A61N 1/044 |

OTHER PUBLICATIONS

Dbees Mobile Application, 2011, http://www.dbees.com/features.php?Ing=gb#id_56 (Year: 2011).*

*Primary Examiner* — Phillip A Gray
*Assistant Examiner* — Rachel T. Smith
(74) *Attorney, Agent, or Firm* — PatentPC PowerPatent; Bao Tran

(57) ABSTRACT

Provided are a method, apparatus, and computer program for providing a notification according to a period of use of a drug infusion device. A time point at which the drug infusion device switches from an inactive mode to an active mode may be determined as a use start time point. Also, an impending expiration notification indicating that expiration of a period of use of the drug infusion device is imminent may be provided at a first time point after a certain period from the use start time point, based on a usable period and a user set time of the drug infusion device. In addition, an expiration notification indicating that the period of use of the drug infusion device has expired may be provided at a second time point after the usable period from the use start time point.

16 Claims, 12 Drawing Sheets

(58) Field of Classification Search
CPC .... A61M 2205/3592; A61M 2205/583; A61M 2230/201; A61M 5/14248; G16H 20/17; G16H 40/20; H04W 12/03; H04W 12/63; H04W 12/71
See application file for complete search history.

(56) References Cited

U.S. PATENT DOCUMENTS

| | | | |
|---|---|---|---|
| 2011/0257798 A1* | 10/2011 | Ali | G06F 11/0796 |
| | | | 700/282 |
| 2012/0316506 A1* | 12/2012 | Sonderegger | A61M 5/1626 |
| | | | 604/180 |
| 2018/0221636 A1* | 8/2018 | Stein | A61N 1/325 |

* cited by examiner

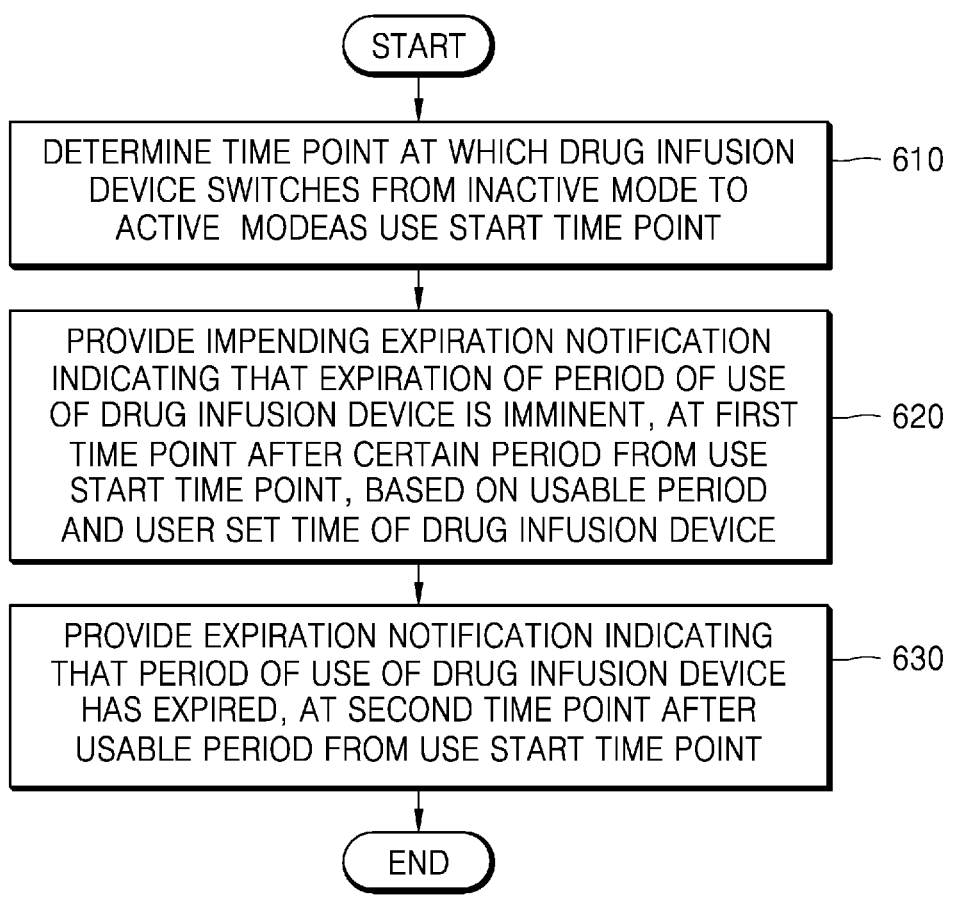

SYSTEMS AND METHODS FOR MANAGING DIABETES

BACKGROUND

1. Field

The present disclosure relates to a method, apparatus, and computer program product for providing a notification according to a period of use of a drug infusion device.

2. Description of the Related Art

The present application relates to disease management such as diabetes management.

Diabetes is a disease that can be managed by patients. The better the patient manages blood glucose level, the more likely he/she can prevent the host of complications that accompany the disease, such as eye damages or foot damages. Yet, the burden of constantly trying to manage blood sugar is sometimes too much for the patient.

For example, many wearable disposable insulin pump devices in the market today are designed to be worn for no more than 80 hours; usually intended for a three-days' usage life or less, with some extra usage hours in case of emergency. With these systems, the changing cycle always varies; from Monday to Thursday to Sunday to Wednesday, etc. for example. Because of the lack of periodicity, users often forget when they need to change the wearable infusion device (patch), sometimes resulting in missing doses for an extended period of time, and therefore poor compliance.

Diabetes is a metabolic disorder that causes symptoms where blood sugar is out of a normal range because secretion of insulin is insufficient or a normal function is not performed. The diabetes is a complex disease that has potential for affecting each tissue of a human body due to complications such as blindness, kidney failure, heart failure, and neuropathy, and the number of diabetic patients is said to be increasing every year.

In the case of the diabetes, it is necessary to measure the blood sugar by using a blood glucose meter and manage the blood sugar through an appropriate means such as a diet, an exercise program, an insulin injection, an oral diabetes medication, or the like.

In recent years, a technology for automatically infusing insulin to a diabetic patient by using a drug infusion device is being studied, and a technology capable of effectively notifying a user of a period of use of the drug infusion device is required.

SUMMARY

In one aspect, a method to dispense medication using one or more fillable medical dispensers by providing the medical dispenser with a first predetermined medication dosage sufficient for a first predetermined dispensing period, wherein the first dispensing period ends on a first repetitive day of the week for ease of remembrance by a user; providing the medical dispenser with a second predetermined medication dosage sufficient for a second predetermined dispensing period, wherein the dispensing period ends on a second repetitive day of the week for ease of remembrance; and installing the medical dispenser at least twice a week at a repetitive weekly replacement schedule.

Implementations of the above aspect can include one or more of the following. The system can have a first patch with a four-day replacement cycle with a second patch having a three-day replacement cycle, or vice versa. For example, a first patch can be used every Monday morning and a second patch every Thursday evening. Alternatively, the patches can be set up for use every Tuesday morning and every Friday evening, every Wednesday morning and every Saturday evening, every Thursday morning and every Sunday evening, every Friday morning and every Monday evening, every Saturday morning and every Tuesday evening, or every Sunday morning and every Wednesday evening, for example. The system can communicate with the controller at the time of the change and setting an expiry time in the patch with the time set in the controller. The patch can send an alert to the user at a predetermined time prior to the expiry time. The system can disable the patch at the expiry time even if the controller is not near the patch or the communication between the patch and the controller is lost. The system can render a bar graph, pie chart, or a pictorial presentation each representing a week with a pointer where a change interval is adjusted by sliding the pointer to position that represents the time of the week when the patch changes should occur. The system includes setting regular weekly change intervals where each of the intervals is below a predetermined time period, and can also include setting a patch from having the regular weekly change interval to a second predetermined time period.

In other implementations, the medical dispenser communicates with a remote controller such as a smart phone, among others. The method includes communicating with the remote controller at the time of the change and setting an expiry time in the medical dispenser with the time set in the remote controller. The remote controller can receive from the medical dispenser an alert to the user at a predetermined time prior to the expiry time. The system can disable the medical dispenser at an expiry time even if the remote controller is not near the patch or if contact with the remote controller is lost. The system can encrypt communications between the remote controller and the medical dispenser. The encryption of the communications between the remote controller and the medical dispenser can be based on a patient identifier or an EMEI (International Mobile Equipment Identity). The method includes providing Continuous Glucose Monitoring (CGM) of the user. The system can automatically provide a bolus based on the CGM after losing contact with the remote controller for a predetermined period. Alternatively, the system can confirm with the user before providing a bolus based on the CGM if a user glucose trend indicates a need for the bolus.

Advantages of the system may include one or more of the following. The system helps patients achieve high insulin compliance and can prevent complications arising from diabetes, such as blindness, kidney failures or loss of toes. High compliance is achieved because the system provides regularity in the patch changing intervals on weekly basis, such as, for examples, every Monday morning and Wednesday evening, or every Sunday morning at 9 am and Thursday morning at 7 am. This regularity can be achieved if the patch can be used for up to 4 days (or, to be more exact, 84 hours or longer) rather than for 80 hours. This way, for example, a device can be worn for four days, then the next one for three days, or every 84 hours such as every Saturday morning at 9 am and every Tuesday evening at 9 pm, and so on in order to maintain weekly regularity on the changing intervals. However, it is recommended by medical authorities such as Center for Disease Control that needles and/or cannulas be changed every 3 days in order to minimize any chance of developing infection on/around the infusion site of a user's body. Also, users may be tempted to use the device for the full four days every time in order to reduce the number of devices needed to be purchased or simply because of lack of attention. This will substantially increase the adverse chance of developing infection on the infusion area of the body. Thus, to comply with the professional recommendation as closely as possible and minimize the chance of developing infection while still maintaining a weekly regularity of changing terms, the pairing controller can limit the changing interval time. For example, the controller may be programmed to have a 'weekly regular replacement' feature that allows a user to preset the regular weekly change intervals such that each of the intervals is no more than, for example, 90 hours, while those devices not changed under this weekly regular replacement feature will be set to expire after three days or 80 hours, like many other wearable devices do today. The weekly regular replacement feature may include a bar graph, pie chart, or other pictorial presentations that each represents a week with a pointer such that the change interval can be adjusted by the sliding of the pointer to the position that represents the time of the week when the patch changes should occur.

Additionally, the wearable device (patch) can also be programmed so that it communicates with the controller at the time of the change and preset the time inside the patch firmware so that the patch expires at the same time set in the controller. This way, the patch can alert the user at predetermined time prior to the expiry time, and also shut down the patch at the expiry time even if a controller is not located near the patch or the communication between the patch and the controller is lost.

Provided are a method, apparatus, and computer program for providing a notification according to a period of use of a drug infusion device.

Additional aspects will be set forth in part in the description which follows and, in part, will be apparent from the description, or may be learned by practice of the presented embodiments of the disclosure.

According to an aspect of the disclosure, there is provided a method of providing a notification according to a period of use of a drug infusion device, including: determining a time point at which the drug infusion device switches from an inactive mode to an active mode as a use start time point; providing an impending expiration notification indicating that expiration of the period of use of the drug infusion device is imminent at a first time point after a certain period from the use start time point, based on a usable period and a user set time of the drug infusion device; and providing an expiration notification indicating that the period of use of the drug infusion device has expired at a second time point after the usable period from the use start time point.

According to another aspect of the present disclosure, there is provided an apparatus for providing a notification according to a period of use of a drug infusion device, including: a memory storing at least one program; and a processor configured to perform an operation by executing the at least one program, wherein the processor determines a time point at which the drug infusion device switches from an inactive mode to an active mode as a use start time point, provides an impending expiration notification indicating that expiration of the period of use of the drug infusion device is imminent at a first-time point after a certain period from the use start time point, based on a usable period and a user set time of the drug infusion device and provides an expiration notification indicating that the period of use of the drug infusion device has expired at a second-time point after the usable period from the use start time point.

According to another aspect of the present disclosure, there is provided a computer program product including at least one computer-readable recording medium storing a program for executing: determining a time point at which a drug infusion device switches from an inactive mode to an active mode as a use start time point; providing an impending replacement notification of the drug infusion device at a first-time point after a certain period from the use start time point, based on a usable period and a user set time of the drug infusion device; and providing an expiration notification indicating that a period of use of the drug infusion device has expired at a second point after the usable period from the use start time point.

BRIEF DESCRIPTION OF THE DRAWINGS

FIG. 8 is a flowchart of a method of providing a notification according to a period of use of a drug infusion device, according to an embodiment.

DETAILED DESCRIPTION

Figure 1A:
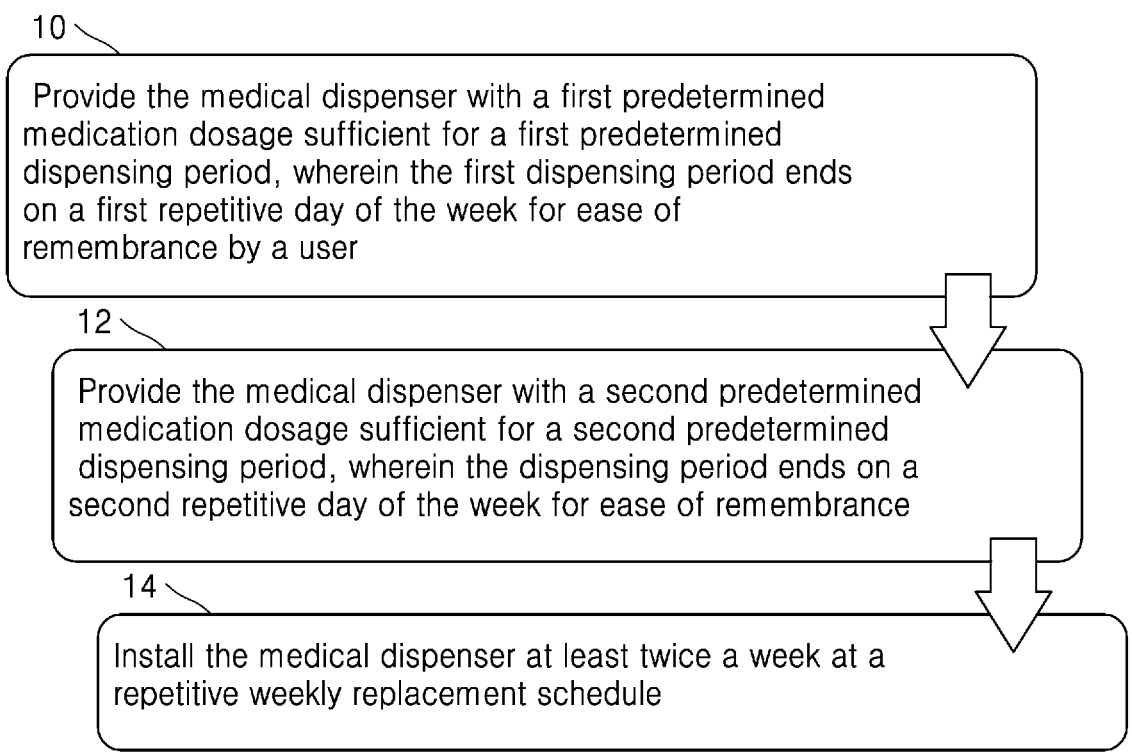
FIGS. 1A-1D illustrate exemplary processes for managing insulin dispensing in the wearable automated medication delivery system.
Figure 1B:
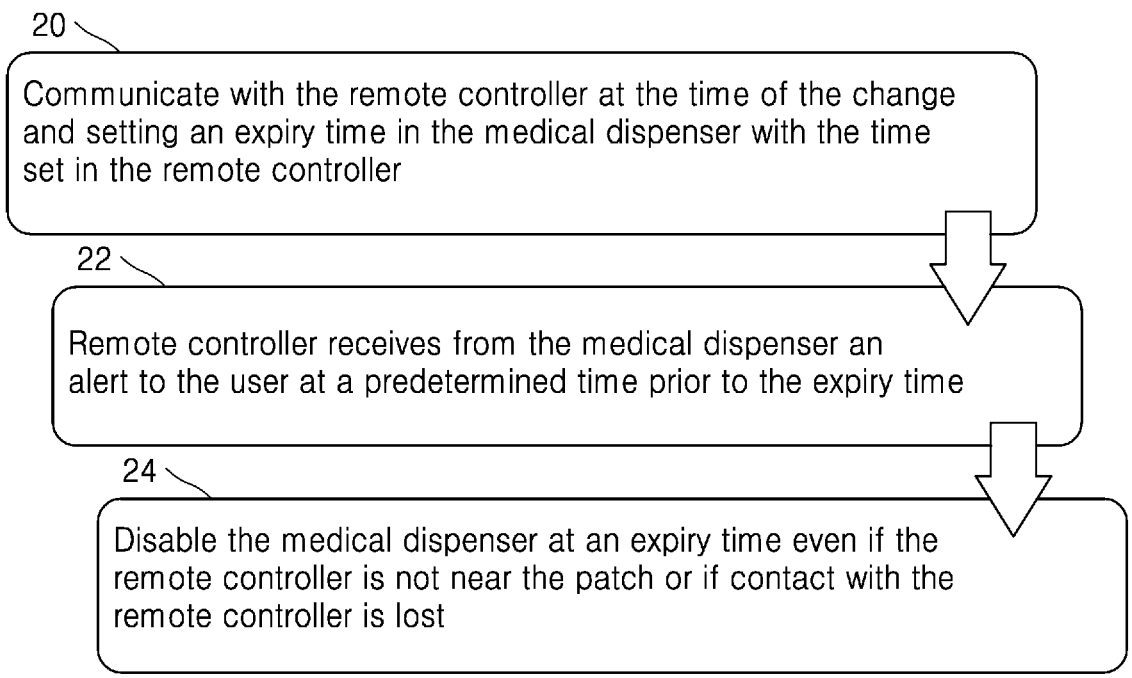
Figure 1C:
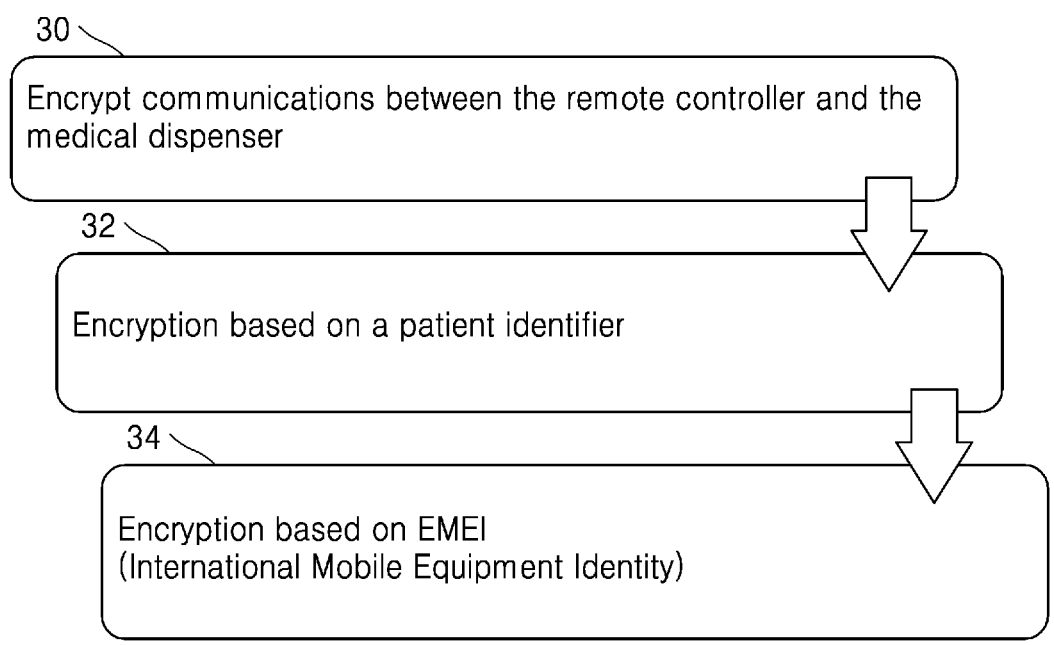

Hereinafter, embodiments of the present disclosure will be described in detail with reference to the accompanying drawings such that one of ordinary skill in the art may easily implement the present disclosure. However, the present disclosure may be implemented in various different forms and is not limited to embodiments described herein. Also, in the drawings, parts irrelevant to the description are omitted in order to clearly describe the present disclosure, and like reference numerals designate like elements throughout the specification.

Throughout the specification, when a part is "connected" to another part, the part may not only be "directly connected" to the other part, but may also be "electrically connected" to the other part with another element in between. In addition, when a part "includes" a certain element, the part may further include another element instead of excluding the other element, unless otherwise stated.

Hereinafter, the present disclosure will be described in detail with reference to accompanying drawings.

FIG. 1 shows an exemplary process to manage insulin replacement for an insulin device 102 (FIG. 2) which can be wearable device or a patch, among others. The process simplifies and regularizes the refill or replacement of the insulin delivery device 102 with an insulin capacity of less than a week. While the medical device insulin capacity can be increased to last exactly one week so that the refill or replacement always end on a particular day of the week for ease of remembering, this is not preferred since medical professionals prefer that needles and/or cannulas be changed every 3 days in order to minimize any chance of developing infection on/around the infusion site of a user's body.

For users it can be difficult to remember to refill or replace insulin dispensing devices on different days of the week. To help the user remember to refill or replace the insulin, the instant system splits the replacement or refill cycle into two or more events that occur on exactly the same days of the week so that users can easily remember when to replace or refill the device 102. Thus, to comply with the professional recommendation as closely as possible, to minimize the chance of developing infection, and to maintain regularity in replenishment events, a controller in the device 102 (FIG. 2) can apply the process of FIG. 1 in changing interval time. For example, the controller may be programmed to have a 'weekly regular replacement' feature that allows a user to preset the regular weekly change intervals such that each of the intervals is no more than, for example, 90 hours, while those devices not changed under this weekly regular replacement feature will be set to expire after three days or 80 hours, like many other wearable devices do today.

The weekly regular replacement feature may include a bar graph, pie chart, or other pictorial presentations that each represents a week with a pointer such that the change interval can be adjusted by the sliding of the pointer to the position that represents the time of the week when the patch changes should occur.

The refill or replacement cycle occurring on repetitive and specific day(s) of the week provides a consistency and ease of remembrance for the user. In one example, if the user changes the device 102 every Monday morning and every Thursday evening, it will become a natural weekly routine for users. Since the filling syringe can provide dosages for up to 4 days, the system ensures that the device 102 is refilled or replenished in a timely manner to ensure correct patient treatment.

The process of FIG. 1A includes the following:
  Provide the medical dispenser with a first predetermined medication dosage sufficient for a first predetermined dispensing period, wherein the first dispensing period ends on a first repetitive day of the week for ease of remembrance by a user (10)
  Provide the medical dispenser with a second predetermined medication dosage sufficient for a second predetermined dispensing period, wherein the dispensing period ends on a second repetitive day of the week for ease of remembrance (12)
  Install the medical dispenser at least twice a week at a repetitive weekly replacement schedule (14)

Additionally, the wearable device (patch) can also be programmed so that it communicates with the controller at the time of the change and preset the time inside the patch firmware so that the patch expires at the same time set in the controller. This way, the patch can alert the user at predetermined time prior to the expiry time, and also shut down the device/patch at the expiry time even if a controller is not located near the device. This process is illustrated in FIG. 4B as follows:
  Communicate with the remote controller at the time of the change and setting an expiry time in the medical dispenser with the time set in the remote controller (20)
  Remote controller receives from the medical dispenser an alert to the user at a predetermined time prior to the expiry time (22)
  Disable the medical dispenser at an expiry time even if the remote controller is not near the patch or if contact with the remote controller is lost (24)

In operation 24, the device 102 is programmed to automatically turn off after a set interval by the user, for example after 24 hours of no connectivity with the remote controller. In that case, the device 102 will shut off for safety reasons if there are no communications for any reason.

In one embodiment, to provide enhanced security in the communications between the controller and the device 102, one embodiment uses a unique encryption between a particular phone by pairing the phone's unique number such as an EMEI (International Mobile Equipment Identity) number with the dispensing device 102. The user can find the IMEI by entering *#06# on the phone's call screen. You can also find it in your phone's settings or by inspecting the back of your phone, or underneath your phone's battery, or in the phone settings tab. In this embodiment, the device 102 would only accept commands from a phone with a matching EMEI number. This process is shown in FIG. 10 as follows:
  Encrypt communications between the remote controller and the medical dispenser (30)
  Encryption based on a patient identifier (32)
  Encryption based on EMEI (International Mobile Equipment Identity) (34)

In the alternative of step 34, the device 102 is encrypted with a unique id that belongs to a particular patient number, and the app would transmit messages encrypted with the unique patient ID to ensure that the app is securely communicating with the right device with the right commands.

Figure 1D:
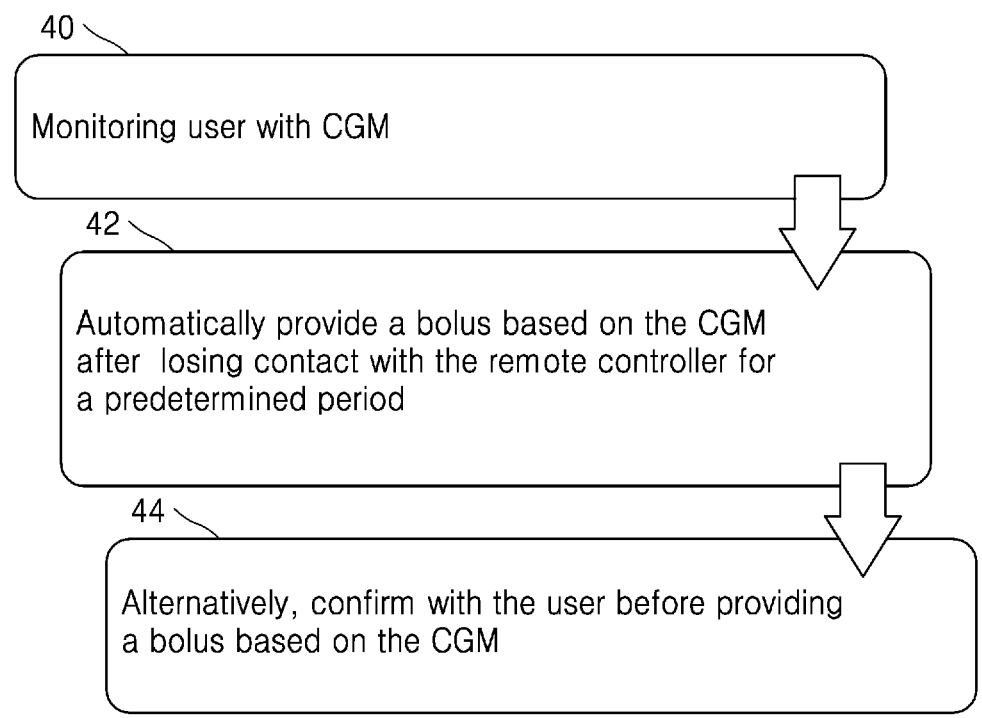

In another embodiment, the device 102 provides an automatic bolus depending on patient history or rapid Continuous Glucose Monitors (CGMs) uptick. CGMs monitor the body's glucose levels in real-time by sensing the glucose present in tissue fluid (also called interstitial fluid). Whereas a meter provides a measurement of the blood glucose at a specific moment in time, the CGM provides an overview of the blood glucose levels over a period of time. Based on the CGM trend, the device 102 can warn users if they are trending towards hypo or hyperglycemia. They are particularly useful at night, as they can sound an alert if glucose levels drop. CGMs may need to be calibrated with a fingerstick blood sugar reading for optimal sensor accuracy. In one exemplary operation, if a time lapse exceeds 12-16 hrs and the patient has forgotten or lost communication with the controller, the device 102 provides an additional bolus after confirming with the user. In other embodiments, the bolus can be provided automatically to the user, and a warning can be sent to caregivers of the user or medical professionals caring for the user. One implementation is shown in FIG. 1D as follows:
  Monitoring user with CGM (40)
  Automatically provide a bolus based on the CGM after losing contact with the remote controller fora predetermined period (42)
  Alternatively, confirm with the user before providing a bolus based on the CGM (44)

Figure 2:
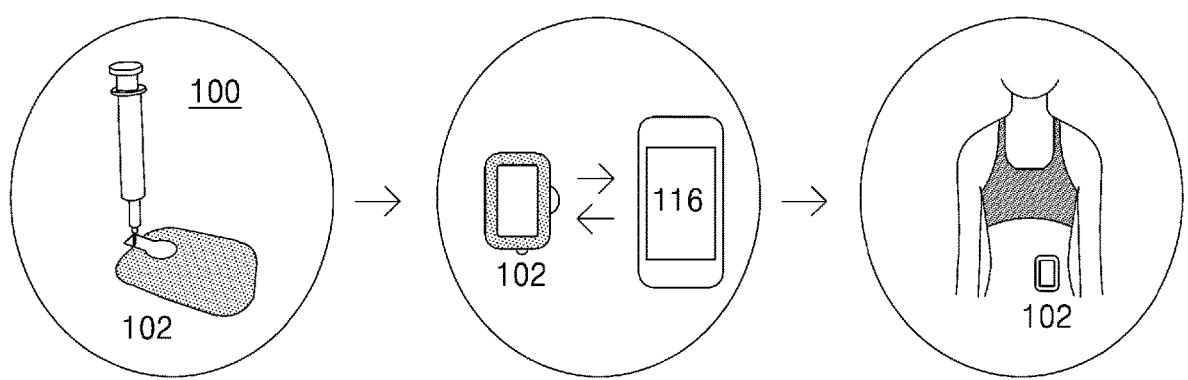
FIG. 2 illustrates an exemplary wearable automated medication delivery system (medical dispenser).

FIG. 2 illustrates an exemplary dispensing device which can be a wearable disposable insulin pump or patch as a wearable automated medication delivery system 100. To use the device of FIG. 2, the user first applies a filling syringe found in a pump packet to fill Patch or medical device 102 with insulin. Next, the user follows instructions provided on the paired controller to activate a new Patch 102. The user can then apply the new Patch 102. The wearable automated medication delivery system 100 can include a medical device 102. The medical device 102 can be attached to the body of a user and can deliver a medication to the user. The medical device 102 can be a wearable device. In particular, the medical device 102 can be directly coupled to a user (e.g., directly attached to a body part and/or skin of the user). A surface of the medical device 102 can include an adhesive to facilitate attachment to the user. The medical device 102 can include a number of components to facilitate automated delivery of a medication to the user. For example, the medical device 102 can include a reservoir for storing the medication, a needle or cannula for delivering the medication into the body of the person, and a pump for transferring the medication from the reservoir, through the needle or cannula, into the body of the user. The medical device 102 can also include a power source such as a battery for supplying power to the pump and/or other components of the medical device 102. The medical device 102 can store and provide any medication or drug to the user. In various embodiments, the medical device 102 can be an automated wearable insulin delivery device. For example, the medical device 102 can be the EOPatch wearable insulin pump system, with the thin and light disposable pump unit (Patch), and the smart-phone like color touchscreen controller (ADM) together with the advanced managing software tools, is designed to reduce the burden of insulin management, and make the user's life a little bit easier.

In general, the system can automatically monitor glucose levels of the user, automatically determine a delivery of insulin to the user based on the monitored glucose levels, and automatically provide the determined amount of insulin to the user. Each of these steps can be performed without any user input or interaction. In various embodiments, a user confirmation can be required before the insulin is provided to the user as discussed above. For example, when handheld electronic computing device 116 is implemented as a cellphone, for added security, the user can be required to confirm or acknowledge the determined delivery of insulin to the user. Without receiving such confirmation, the delivery can be blocked or prevented. This security feature can mitigate hacking or other cybersecurity risks.

As discussed above, the wearable insulin delivery device 102 can include one or more user output devices that can be used to provide an alarm, alert, notification, or indication to the user that an instruction for insulin delivery has been determined or received. This indication can be audible, visual, and/or vibrational for example. In various embodiments, the indication can include one or more flashing light emitting diodes and/or a vibration provided by the wearable insulin delivery device 102. One or more user input devices provided with the wearable insulin delivery device 102 can be used to provide a required confirmation from the user. The input devices can include a button, a touch screen, or an accelerometer (e.g., such that the input can be a tapping or movement of the wearable insulin delivery device 102). Although user input may be needed to ensure the final step of providing the determined level of insulin to the user occurs, such embodiments can be considered as largely automatic with one or more added security features for the user.

The medical device 102 can also contain analog and/or digital circuitry for controlling the delivery of the medication. The circuitry can be implemented as a controller. The circuitry can include discrete, specialized logic and/or components, an application-specific integrated circuit, a microcontroller or processor that executes software instructions, firmware, or any combination thereof. In various embodiments, the control circuitry can be configured to cause the pump to deliver doses of the medication to the person at predetermined intervals. The size and/or timing of the doses may be programmed into the control circuitry using a wired or wireless link by the user or by a third party (such as a health care provider).

Instructions for determining the delivery of the medication to the user (e.g., the size and/or timing of any doses of the medication) can originate locally (e.g., based on determinations made by the medical device 102) or can originate remotely and then provided to the medical device 102. Remote instructions can be provided to the medical device 102 over a wired or wireless link. The medical device 102 can execute any received instructions for the delivery of the medication to the user. In this way, under either scenario, the delivery of the medication to the user can be automated.

In various embodiments, the medical device 102 can communicate via a wireless link 104 with an electronic device 116. The electronic device 116 can be any electronic device such as, for example, an Apple Watch. The electronic device 116 can be a wearable wireless accessory device or can be a smart phone, among others. The wireless link 104 can be any type of wireless link provided by any known wireless standard. As an example, the wireless link can provide communications based on Bluetooth, Wi-Fi, a near-field communication standard, a cellular standard, or any other wireless protocol. The control circuitry in the medical device 102 may include circuitry implementing a wireless transmitter, receiver, and/or transceiver for communication over the link 104 or 122. Information may be transmitted between the medical device 102 and the electronic device 116 over the link 104 and/or between the medical device 102 over the link 122. The shared information may include handshake/pairing information, data, commands, status information, or any other such information.

In various embodiments, the electronic device 116 transmits a command to the medical device 102 that specifies an action for the medical device 102 to take regarding delivery of the medication. In another embodiment, the sensor sends a signal to the medical device 102 via the link 122, and the medical device 102 executes an algorithm to determine an action for the medical device 102 to take regarding delivery of the medication. The action may be delivery of a bolus of the medication, a change in a time, frequency, or schedule of future deliveries of the medication, a change in a size of future deliveries of the medication, or any other such action. The command may further comprise a bolus size, a bolus time, or any other such additional information. The medical device 102 may transmit a confirmation message back to the electronic device 116 upon receipt of the command and/or after completion of the action.

In various embodiments, the electronic device 116 transmits the command as specified by an algorithm executing thereon, such as an insulin bolus injection algorithm. The algorithm may execute in the context of a software application running on the electronic device. The user may download this application from an application store, such as the Apple iTunes store, or from any other source. The algorithm may be used to compute appropriate times and doses of delivery of the medication. In some embodiments, the algorithm bases these computations at least in part on information known about the person, such as sex, age, weight, or height, and/or on information gathered about a physical attribute or condition of the person (e.g., from the sensor). For example, the algorithm may determine an appropriate delivery of the medication based on glucose level monitoring of the user. The software application may further permit the person to access status information regarding the medical device 102, such as its battery level, number of doses remaining, amount of time in use, or other such status information. The software application may instead or in addition allow the person to issue commands to the medical device 102, such as a command to deliver a bolus.

In various embodiments, a sensor is worn on the body of the person or implanted within the person and is used to collect information regarding one or more physical attributes or conditions of the person. The sensor can be coupled to the user and worn on a body part of the user. The sensor can be a glucose sensor. For example, the sensor can be a continuous glucose monitor (CGM). Although the sensor is depicted as separate from the medical device 102, in various embodiments, the sensor and medical device 102 may be incorporated into the same unit. That is, in various embodiments, the sensor can be a part of the medical device 102 and contained within the same housing of the medical device 102 (e.g., the sensor can be positioned within or embedded within the medical device).

The sensor can include one or more sensing elements, an electronic transmitter, receiver, and/or transceiver for communicating with the electronic device 116 over a wired/wireless link or with medical device 102 over the link. The sensor can also include a power source for supplying power to the sensing elements and/or transceiver. Communications provided by the sensor may include data gathered from the sensing elements. This data can be transmitted continually, at periodic intervals, and/or during or after a change in sensed data (e.g., if a glucose level or rate of change in the level exceeds a threshold). The software application executing the algorithm may use this collected information to send a command to the medical device 102 to, for example, deliver a bolus to the person, change the amount or timing of future doses, or other commands.

The electronic device 116 can be considered to be a wireless accessory device or an intermediate device. In various embodiments, the electronic device 116 can relay commands for delivery of a medication from a remote source to the medical device 102. In various embodiments, the electronic device 116 can include a controller for determining delivery of the medication (e.g., the electronic device can include a controller for executing an "artificial pancreas" algorithm). The sensor can be any type of sensor and is not limited to a CGM. The sensor can include one or more sensors housed in the same physical unit.

The electronic device 116 and/or the medical device 102 may communicate with one more remote devices, which may include computers, servers, storage devices, cloud-based services, or other similar devices. The remote device may be owned or operated by, for example, health-care companies or services, pharmacies, doctors, nurses, or other such medically-related entities. The remote device may include a cloud-based data management system. A user may wish, for example, to back up data collected from the sensor, back up a record of medication delivery times and doses provided by the medical device 102, or back up other such information. A wireless link may be used to connect the electronic device 116 to the remote devices and/or a wireless link may be used to connect the medical device 102 to the remote devices.

Alternatively or in addition thereto, the electronic device 116 may communicate with a local device. The local device can be a dedicated control or monitoring device (e.g., a diabetes management device and/or a custom handheld electronic computing device), cellular phone, laptop computer, tablet, desktop computer, or other similar electronic computing device. The local device can communicate with the electronic device 116 over a wireless link. The wireless link can be of the same type as the other wireless links described herein.

A software application executing on the local device may be used to send commands to the medical device 102 (e.g., via the electronic device) and/or receive status information about the medical device 102 (e.g., via the electronic device). In other embodiments, the local device instead or in addition communicates directly via a wireless link with the medical device 102. Additionally, the sensor may communicate via a wireless link with the local device. The local device may communicate with the remote devices via a wireless link.

In general, the system 100 can automatically monitor glucose levels of the user, automatically determine a delivery of insulin to the user based on the monitored glucose levels, and automatically provide the determined amount of insulin to the user. Each of these steps can be performed without any user input or interaction. In various embodiments, a user confirmation can be required before the insulin is provided to the user as discussed above. For example, when handheld electronic computing device 102 is implemented as a cellphone, for added security, the user can be required to confirm or acknowledge the determined delivery of insulin to the user. Without receiving such confirmation, the delivery can be blocked or prevented. This security feature can mitigate hacking or other cybersecurity risks. Additionally, the wearable device (patch) can also be programmed so that it communicates with the controller at the time of the change and preset the time inside the patch firmware so that the patch expires at the same time set in the controller. This way, the patch can alert the user at predetermined time prior to the expiry time, and also shut down the patch at the expiry time even if a controller is not located near the patch or the communication between the patch and the controller is lost.

The system helps patients achieve high insulin compliance and can prevent complications arising from diabetes, such as blindness, kidney failures or loss of toes. High compliance is achieved because the system provides regularity in the patch changing intervals on weekly basis, such as, for examples, every Monday morning and Wednesday evening, or every Sunday morning at 9 am and Thursday morning at 7 am. This regularity can be achieved if the patch can be used for up to 4 days (or, to be more exact, 84 hours or longer) rather than for 80 hours. This way, for example, a device can be worn for four days, then the next one for three days, or every 84 hours such as every Saturday morning at 9 am and every Tuesday evening at 9 pm, and so on in order to maintain weekly regularity on the changing intervals. However, it is recommended by medical authorities such as Center for Disease Control that needles and/or cannulas be changed every 3 days in order to minimize any chance of developing infection on/around the infusion site of a user's body. Also, users may be tempted to use the device for the full four days every time in order to reduce the number of devices needed to be purchased or simply because of lack of attention. This will substantially increase the adverse chance of developing infection on the infusion area of the body. So to comply with the professional recommendation as closely as possible and minimize the chance of developing infection while still maintaining a weekly regularity of changing terms, the pairing controller can limit the changing interval time. For example, the controller may be programmed to have a 'weekly regular replacement' feature that allows a user to preset the regular weekly change intervals such that each of the intervals is no more than, for example, 90 hours, while those devices not changed under this weekly regular replacement feature will be set to expire after three days or 80 hours, like many other wearable devices do today. The weekly regular replacement feature may include a bar graph, pie chart, or other pictorial presentations that each represents a week with a pointer such that the change interval can be adjusted by the sliding of the pointer to the position that represents the time of the week when the patch changes should occur.

As discussed above, the wearable insulin delivery device 102 can include one or more user output devices that can be used to provide an alarm, alert, notification, or indication to the user that an instruction for insulin delivery has been determined or received. This indication can be audible, visual, and/or vibrational for example. In various embodiments, the indication can include one or more flashing light emitting diodes and/or a vibration provided by the wearable insulin delivery device 102. One or more user input devices provided with the wearable insulin delivery device 102 can be used to provide a required confirmation from the user. The input devices can include a button, a touch screen, or an accelerometer (e.g., such that the input can be a tapping or movement of the wearable insulin delivery device 102). Although user input may be needed to ensure the final step of providing the determined level of insulin to the user occurs, such embodiments can be considered as largely automatic with one or more added security features for the user.

Various embodiments include systems and methods for delivering a medication to a person using a wearable medical device in accordance with a wireless signal received from an electronic device. In various embodiments, the electronic device is a smart watch, smart necklace, module attached to the medical device, or any other type or sort of electronic device that may be worn or carried on the body of the person and executes an algorithm that computes the times and dosages of delivery of the medication. For example, the electronic device may execute an artificial-pancreas algorithm that computes the times and dosages of delivery of insulin. The electronic device may also be in communication with a sensor, such as a glucose sensor, that collects data on a physical attribute or condition of the person, such as a glucose level. The sensor may be disposed in or on the body of the person and may be part of the medical device or may be a separate device. Alternately, the medical device may be in communication with the sensor in lieu of or in addition to the communication between the sensor and the electronic device. The communication may be direct (if, e.g., the sensor is integrated with or otherwise a part of the medical device) or remote/wireless (if, e.g., the sensor is disposed in a different housing than the medical device). In these embodiments, the sensor and/or medical device contains computing hardware (e.g., a processor, memory, firmware, etc.) that executes some or all of the algorithm that computes the times and dosages of delivery of the medication.

Various embodiments described herein include systems and methods for automatically delivering medication to a user. A sensor coupled to a user can collect information regarding the user. A controller can use the collected information to determine an amount of medication to provide the user. The controller can instruct a drug delivery device to dispense the medication to the user. The drug delivery device can be a wearable insulin pump that is directly coupled to the user. The controller can be part of or implemented in a cellphone. A user can be required to provide a confirmation input to allow a determined amount of insulin to be provided to the user based on detected glucose levels of the user.

Certain embodiments of the present invention were described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description. Further, many of the techniques and embodiments described are not limited to the delivery of insulin but are applicable to the automated delivery of any medication to a user.

Figure 3:
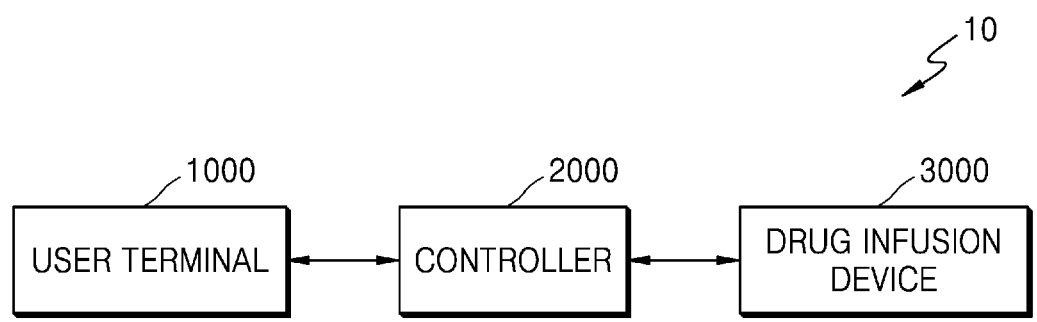
FIG. 3 is a block diagram of an insulin management system including a user terminal, a controller, and a drug infusion device.

FIG. 3 is a block diagram of an insulin management system 10, including a user terminal 1000, a controller 2000, and a drug infusion device 3000.

The user terminal 1000 denotes a communication terminal capable of using a web service in a wired/wireless communication environment. For example, the user terminal 1000 may be a smartphone, a tablet personal computer (PC), a PC, a smart television (TV), a mobile phone, a personal digital assistant (PDA), a laptop computer, a media player, a micro-server, a global positioning system (GPS) device, an electronic book terminal, a digital broadcasting terminal, a navigation device, a kiosk, an MP3 player, a digital camera, a home appliance, a device equipped with a camera, or another mobile or non-mobile computing device. Also, the user terminal 1000 may be a wearable device, such as a watch, glasses, a hairband, or a ring, having a communication function and a data processing function. However, a terminal equipped with an application capable of Internet communication as described above may be unlimitedly employed.

The user terminal 1000 may be connected to a pre-registered controller 2000 on a one-to-one basis. Also, the user terminal 1000 may receive data from the controller 2000 so as to prevent control by an external apparatus. The user terminal 1000 may transmit, to the controller 2000, configuration information, for example, system time information, within a pre-set range.

The controller 2000 performs a function of transmitting/receiving data to/from the drug infusion device 3000, and may transmit a control signal related to infusion of a drug, such as insulin, to the drug infusion device 3000, and receive a control signal related to the measurement of a biometric value, such as blood sugar, from the drug infusion device 3000.

The controller 2000 may transmit an instruction request for measuring a current state of a user to the drug infusion device 3000 and receive measurement data from the drug infusion device 3000 in response to the instruction request.

Here, the drug infusion device 3000 performs the function of measuring a biometric value, such as a blood sugar value, blood pressure, or a heart rate of the user, and may also perform a function of infusing a drug, such as insulin, glucagon, anesthetic, pain reliever, dopamine, growth hormone, or smoking cessation aid, which is to be infused to the user.

The drug infusion device 3000 may further include a storage portion storing a substance to be periodically infused to the user. It may be controlled such that an infusion amount to be infused according to an infusion signal generated by the controller 2000 is infused from the storage portion.

Here, the drug infusion device 3000 may transmit, to the controller 2000, information, such as a measured value and the infusion amount. Selectively, the drug infusion device 3000 may transmit, to the controller 2000, a device state message, a biometric value measurement message, a drug infusion message, or the like. For example, the drug infusion device 3000 may transmit, to the controller 2000, the device state message including remaining battery capacity information of a device, whether a device is booted successfully, whether infusion is successful, or the like. Messages transmitted to the controller 2000 may be transmitted to the user terminal 1000 via the controller 2000. Alternatively, the controller 2000 may transmit, to the user terminal 1000, improved data obtained by processing the received message.

The drug infusion device 3000 may also be implemented to communicate only with the pre-registered controller 2000. The drug infusion device 3000 may be classified into a measuring device performing a function of measuring a biometric value, such as a blood sugar value, blood pressure, or a heart rate of the user, and an infusion device performing a function of infusing a drug, such as insulin, glucagon, anesthetic, or the like, in terms of hardware. In other words, the measuring device and an infusion device may be independently present. The controller 2000 may be connected to each of the injection device and the measuring device to generate and provide a control signal for the injection device based on a measured value measured via the measuring device.

Meanwhile, the user terminal 1000, the controller 2000, and the drug infusion device 3000 may perform communication by using a network. For example, the network includes a local area network (LAN), a wide area network (WAN), a value-added network (VAN), a mobile radio communication network, a satellite communication network, or a combination thereof. The network is a data communication network in a comprehensive sense that enables network components to communicate with each other smoothly, and may include a wired Internet, a wireless Internet, or a mobile wireless communication network. Wireless communication may include, for example, wireless LAN (Wi-Fi), Bluetooth, Bluetooth low energy (BLE), Zigbee, Wi-Fi direct (WFD), ultra-wideband (UWB), infrared data association (IrDA), or near field communication (NFC), but is not limited thereto.

Figure 4A:
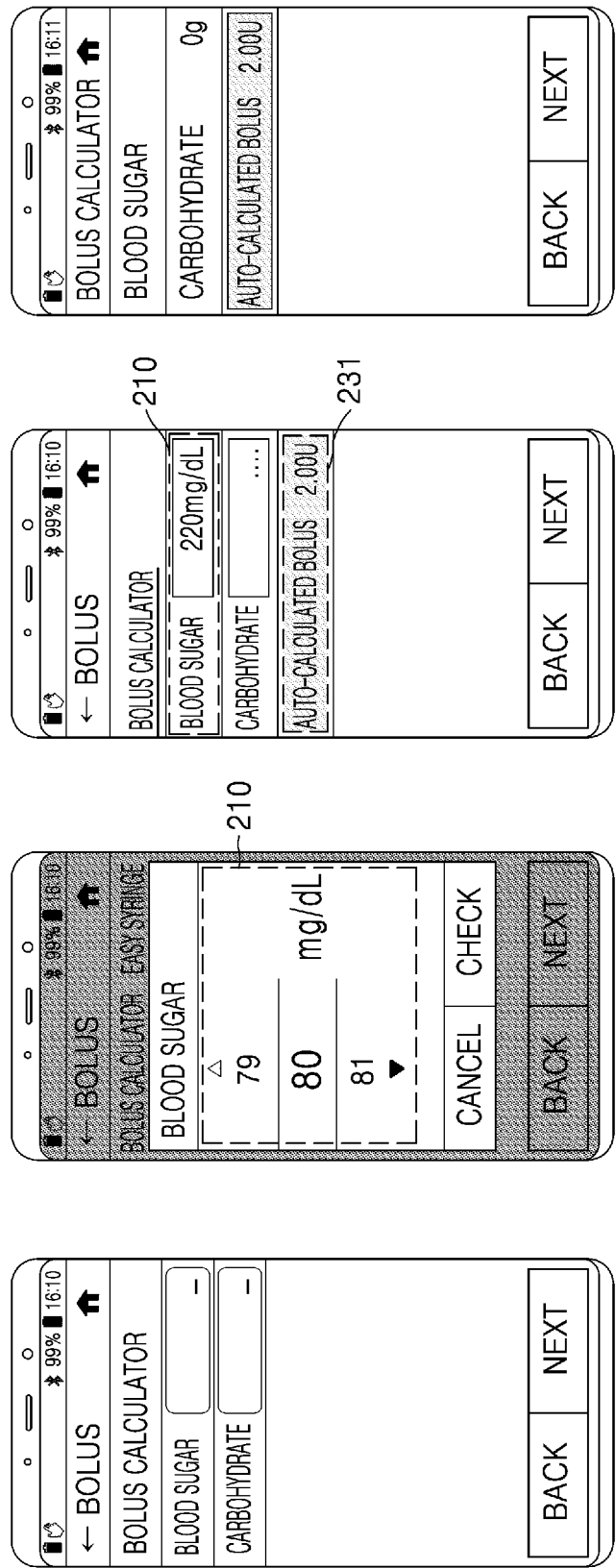
FIGS. 4A and 4B are exemplary diagrams for describing a method of setting a drug infusion amount calculator, according to an embodiment.
Figure 4B:
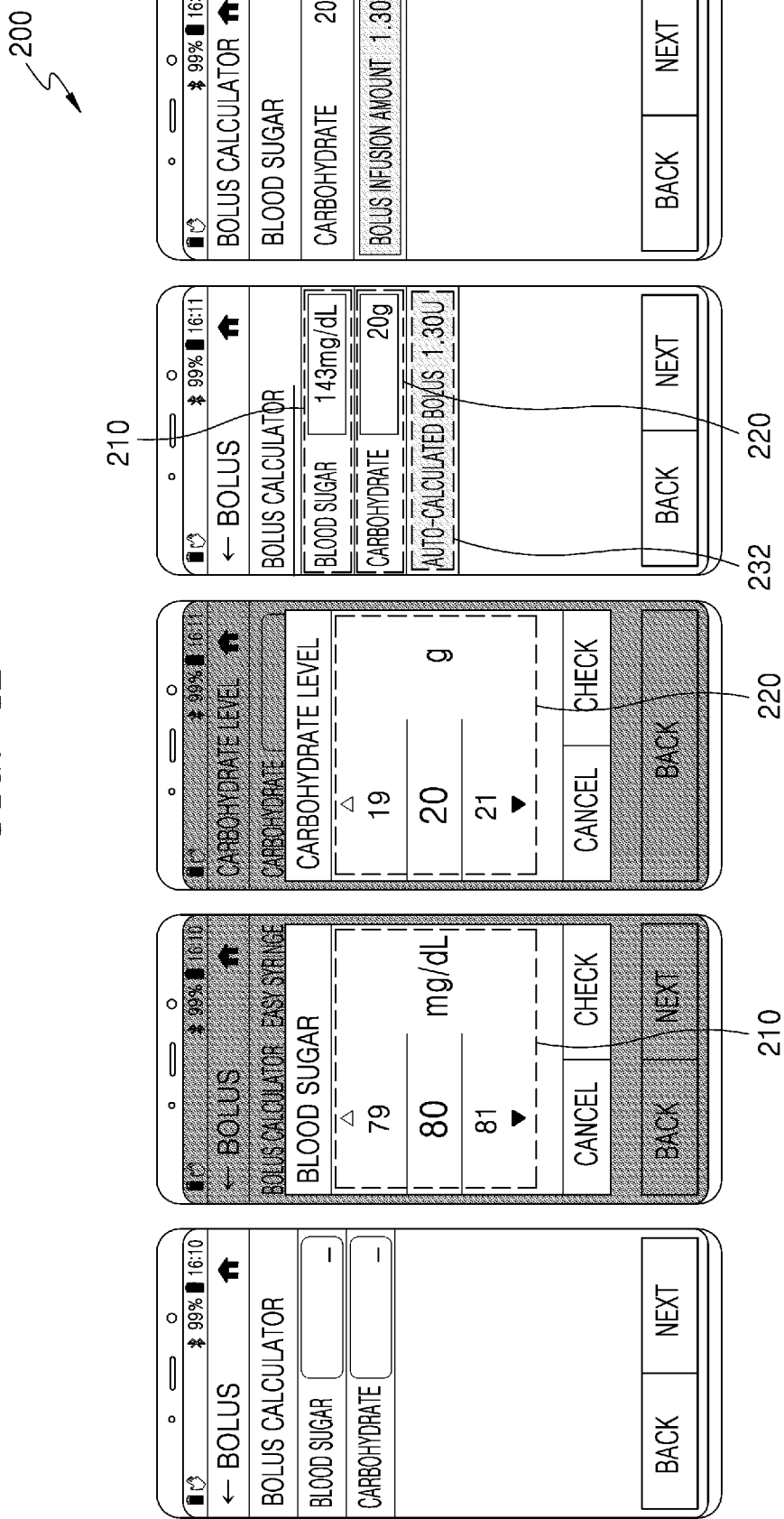

FIGS. 4A and 4B are exemplary diagrams for describing a method of setting a drug infusion amount calculator 200, according to an embodiment.

The drug infusion amount calculator may be provided in the user terminal 1000, controller 2000, or drug infusion device 3000 of FIG. 3. The drug infusion amount calculator may be a calculator that calculates an amount of insulin to be infused to a user separately from initial infusion. For example, the drug infusion amount calculator may calculate an amount of insulin required to decrease blood sugar that increases due to ingestion of food or snack. Also, the drug infusion amount calculator may calculate an amount of insulin required to decrease high blood sugar to a normal blood sugar range.

As described above, insulin infused when food is ingested or when it is required to decrease high blood sugar, separately from the initial infusion of insulin, may be referred to as bolus. The drug infusion amount calculator may be referred to as a bolus calculator, and the bolus calculator may calculate a bolus infusion amount.

The bolus infusion amount may be determined by various values. For example, the bolus infusion amount may be determined by a current blood sugar level, a carbohydrate to insulin ratio, a calibration factor, a target blood sugar level, an amount of insulin with a remaining activation time in a body among a previous bolus infusion amount (insulin on board (IOB), bolus on board (BOB), or active insulin), a calibration threshold value, an amount of activity, or a type and amount of food ingested.

The calibration factor is a value indicating a blood sugar level that may be reduced by 1 unit of bolus insulin. A range of the calibration factor is 1 to 400 mg/dl/U and may be adjusted by 1 mg/dl/U. The calibration threshold value may denote a highest blood sugar value determined to require insulin infusion for blood sugar adjustment.

The bolus calculator may calculate the bolus infusion amount based on a personal bolus profile setting value, a current blood sugar value, an amount of carbohydrate ingested, and IOB of the user.

In detail, the bolus profile setting value may be determined by the target blood sugar, the carbohydrate to insulin ratio, the calibration factor, and insulin duration. The current blood sugar value is a blood sugar value measured within 10 minutes.

Referring to FIG. 4A, the user may input a current blood sugar value 210 to the drug infusion amount calculator. The user may omit an input of an amount of ingested carbohydrate. The user may input the current blood sugar value 210 in mg/dl units. For example, the user may input 220 mg/dl as the current blood sugar value 210. The drug infusion amount calculator may calculate 2.00 U as a bolus infusion amount 231 based on the current blood sugar value 210. A unit for inputting the current blood sugar value 210 may be mmol/l, but the unit is not limited thereto.

Referring to FIG. 4B, the user may input the current blood sugar value 210 and an amount 220 of ingested carbohydrate. The user may input the current blood sugar value 210 in mg/dl units and input the amount 220 of ingested carbohydrate in g units. For example, the user may input 220 mg/dl as the current blood sugar value 210 and input 20 g as the amount 220 of ingested carbohydrate. The drug infusion amount calculator may calculate 1.30 U as a bolus infusion amount 232 based on the current blood sugar value 210 and the amount 220 of ingested carbohydrate.

Figure 5:
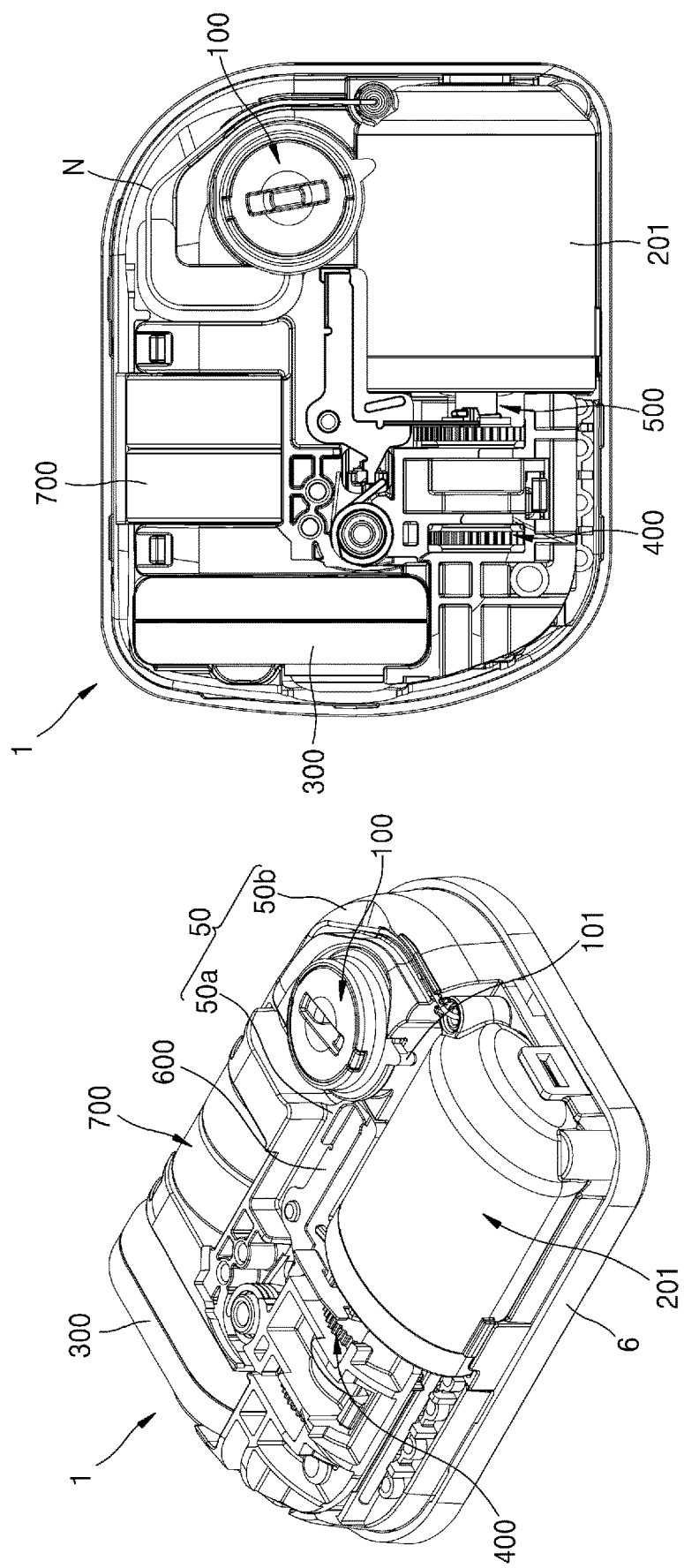
FIG. 5 is a diagram showing an internal configuration of a drug infusion device, according to an embodiment.

FIG. 5 is a diagram showing an internal configuration of a drug infusion device 1, according to an embodiment.

Referring to FIG. 5, the drug infusion device 1 may include a housing 5 covering an outer side and an attaching portion 6 attached to a skin of the user. The drug infusion device 1 includes a plurality of components in an internal space between the housing 5 and the attaching portion 6.

The drug infusion device 1 may include a base body 50, a needle assembly 100, a storage portion 201, a driver 300, a driving unit 400, a clutch unit 500, a trigger member 600, and a battery 700.

The base body 50 forms a basic frame of the housing 5 and is mounted on an inner space of the housing 5. There may be a plurality of base bodies 50. According to an embodiment, a first body 50a covering an upper side of internal components and a second body 50b covering a lower side of the internal components may be provided. The first body 50a and the second body 50b may be assembled to fix the internal components of the drug infusion device 1 at pre-set locations. According to another embodiment, the base body 50 may be formed in one integrated frame.

The storage portion 201 is mounted on the base body 50 and is fluidly connected to the needle assembly 100. A plunger (not shown) may move linearly inside the storage portion 201 to discharge drug to a needle N.

The driver 300 may generate driving power and transmit the driving power to the driving unit 400. The driving power transmitted by the driving unit 400 may linearly move the plunger inside the storage portion 201 so as to discharge the drug.

Any type of pump having drug suction power and drug discharge power by electricity may be used as the driver 300. For example, any type of pump, such as a machine displacement type micropump or an electromagnetic motion type micropump, may be used. The machine displacement type micropump is a pump using motion of a solid or fluid, such as a gear or diaphragm, to create a pressure difference to induce flow of fluid, and may include a diaphragm displacement pump, a fluid displacement pump, a rotary pump, or the like. The electromagnetic motion type micropump is a pump using an electric or magnetic form of energy directly to move fluid, and may include an electro hydrodynamic pump (EHD), an electroosmotic pump, a magneto hydrodynamic pump, an electrowetting pump, or the like.

When the driving unit 400 is engaged by the clutch unit 500, the driver 300 rotates a driving wheel of the driving unit 400, and the plunger may move inside the storage portion 201 as a rod linearly moves according to the rotation of the driving wheel.

The driver 300 may include a membrane arranged inside a cover. The membrane 320 may divide an internal space of the driver 300 into a first space S1 and a second space S2. The driver 300 may linearly move a driving shaft 330 according to a volume change of the first space S1 and second space S2.

Figure 6:
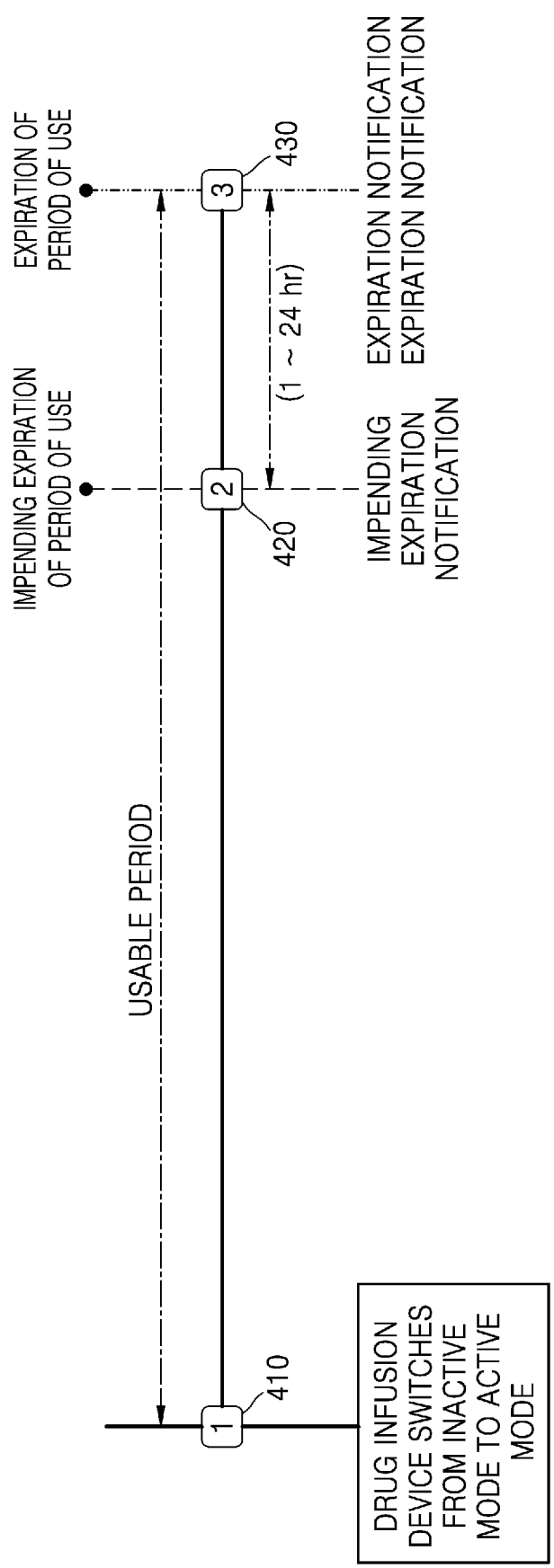
FIG. 6 is a diagram for describing an example of providing a notification according to a period of use of a drug infusion device, according to an embodiment.

FIG. 6 is a diagram for describing an example of providing a notification according to a period of use of a drug infusion device, according to an embodiment.

The drug infusion device may maintain an inactive mode before use, and switch from the inactive mode to an active mode according to a predetermined operation. In the inactive mode of the drug infusion device, power may not be supplied to at least some components in the drug infusion device. In the active mode of the drug infusion device, power may be supplied to a component to which power was not supplied in the inactive mode.

Referring to FIG. 5, according to an embodiment, power may not be supplied to the driver 300 of the drug infusion device 1 in the inactive mode. To discharge the drug stored in the storage portion 201, the driving power of the driver 300 is required, and because power is not supplied to the driver 300 in the inactive mode, the drug stored in the storage portion 201 is not infused to the user. On the other hand, in the active mode, power is supplied to the driver 300 of the drug infusion device 1, and thus the drug stored in the storage portion 201 may be infused to the user.

According to an embodiment, a predetermined operation of switching the drug infusion device 1 from the inactive mode to the active mode may be a drug replenishing operation. The drug infusion device 1 may further include a sensor unit for detecting drug replenishment in the storage portion 201. In detail, when the drug is replenished in the storage portion 201, the plunger connected to a cover of the storage portion 201 may linearly move. A connector member is attached to one side of the plunger, and may move together with the plunger to contact at least a part of the sensor unit. When the connector member contacts at least the part of the sensor unit, the drug infusion device 1 may switch from the inactive mode to the active mode. However, a method by which the drug infusion device 1 switches from the inactive mode to the active mode is not limited thereto.

Referring to FIG. 6, a use start time point 410 indicates a time point at which the drug infusion device switches from the inactive mode to the active mode. For example, a time point at which one end portion of a connector member contacts at least a part of a sensor unit may be the use start time point 410. For example, the drug infusion device may switch from the inactive mode to the active mode when 80 unit or more drug is infused to a patient from the drug infusion device.

A controller transmit/receive data to/from the drug infusion device and control the drug infusion device.

The controller may provide an impending expiration notification indicating that expiration of a period of use of the drug infusion device is imminent at a first time point 420 after a certain period from the use start time point 410, based on a usable period and a user set time of the drug infusion device. For example, the first time point 420 may be set as an arbitrary time point from 1 hour to 24 hours before a time point at which an expiration notification is provided.

In addition, the controller may provide the expiration notification indicating that the period of use of the drug infusion device has expired at a second time point 430 after the usable period from the use start time point 410.

According to an embodiment, the usable period of the drug infusion device may be determined based on at least one of a material of an object maintained being inserted into a body of the user while the drug is infused to the user from the drug infusion device, and a substance (for example, a membrane or the like) coated on the material. According to another embodiment, the usable period of the drug infusion device may be determined based on the structure of the object maintained being inserted into the body of the user while the drug is infused to the user from the drug infusion device. In other words, the usable period of the drug infusion device may be determined based on how long the object can be maintained being inserted into the body of the user without any abnormality.

Referring to FIG. 5, after the drug is stored in the storage portion 201, the drug infusion device 1 is attached to the user. The user attaches the drug infusion device 1 to him/herself and rotates the needle assembly 100 to insert the needle N and cannula into the skin. When the needle N is inserted into the skin together with the cannula, the needle N may induce the cannula to be inserted into the skin.

Thereafter, the needle N is extracted from the skin but maintains being connected to the cannula. When the user further rotates the needle assembly 100, the needle N moves upward while the cannula is inserted into the skin. The cannula and needle N are connected at least partially, and form and maintain a path through which a medical fluid moves.

In other words, the cannula is maintained being inserted into the body of the user while the drug is infused to the user from the storage portion 201, and the drug stored in the storage portion 201 may be infused to the user through the cannula.

As such, when the cannula is maintained being inserted into the body of the user while the drug is infused to the user, the usable period of the drug infusion device may be determined based on a material of the cannula. A period during which safety is guaranteed when the cannula is maintained being inserted into the body may vary depending on the material of the cannula, and thus the usable period of the drug infusion device may be set differently depending on the material of the cannula.

For example, the material of the cannula may include Teflon, and in this case, the usable period of the drug infusion device may be set to 3.5 days. At the second time point 430 after about 3.5 days (84 hours) corresponding to the usable period from the use start time point 410, the controller may provide the expiration notification indicating that the period of use of the drug infusion device has expired. Meanwhile, the usable period may be differently set when the material of the cannula includes another substance in addition to Teflon or includes a substance other than Teflon.

The user may receive the impending expiration notification by setting an arbitrary time before a lapse of the usable period of the drug infusion device. For example, when the usable period of the drug infusion device is set to 3.5 days (84 hours) and the user set time is 1 hour, the controller may provide the impending expiration notification indicating that the expiration of the period of use of the drug infusion device is imminent at the first time point 420 after 83 hours (84 hours−1 hour) from the use start time point 410.

Hereinabove, it has been described that the usable period of the drug infusion device is determined based on the material of the cannula under an assumption that the cannula is maintained being inserted into the body of the user, but the usable period of the drug infusion device may be determined based on a material of the needle N when the needle N is maintained being inserted into the body.

According to another embodiment, the usable period of the drug infusion device may be determined based on capacity of a storage portion and an average daily dosage.

The capacity of the storage portion and the average daily dosage may be indicated in unit units. The unit unit may denote a smallest unit when the drug stored in the storage portion is infused in the body by a pump of a driver.

The average daily dosage may be an average daily dosage calculated by dosage statistics of a plurality of patient, instead of an average daily dosage per each patient. The average daily dosage may vary depending on which type of diabetes a patient has is used to calculate the dosage statistics. For example, an average daily dosage of a patient with type 2 diabetes may be set to be higher than an average daily dosage of a patient with type 1 diabetes.

Also, the average daily dosage may vary depending on concentration of the drug stored in the drug infusion device. For example, the average daily dosage may be set differently when drug containing 100 units in 1 ml is administered to a patient and when drug containing 200 units or 500 units in 1 ml is administered to a patient.

When the capacity of the storage portion is 200 units and the average daily dosage is 60 units, the usable period of the drug infusion device may be set to 3.5 days (200 units/60 units=3.5). In this case, the controller may provide the expiration notification indicating that the period of use of the drug infusion device has expired at the second time point 430 after 3.5 days corresponding to the usable period from the use start time point 410.

Also, the user may receive the impending expiration notification before the usable period is reached by setting an arbitrary time that is before reaching of usable period of the drug infusion device. For example, when the usable period of the drug infusion device is set to 3.5 days (84 hours) and the user set time is 1 hour, the controller may provide the impending expiration notification indicating that the expiration of the period of use of the drug infusion device is imminent at the first time point 420 after 83 hours (84 hours-1 hour) from the use start time point 410.

Meanwhile, when the capacity of the storage portion and the average daily dosage vary, the usable period of the drug infusion device may also vary.

According to another embodiment, the usable period of the drug infusion device may be determined based on the capacity of the storage portion, the average daily dosage, and at least one of the material of the object maintained being inserted into the body of the user while the drug is infused to the user from the drug infusion device, the substance coated on the material, and the structure of the object.

In detail, the controller may determine the usable period of the drug infusion device by comparing a first period during which safety is guaranteed when the cannula is maintained being inserted into the body and a second period calculated based on the capacity of the storage portion and the average daily dosage.

For example, when the first period during which safety is guaranteed when the cannula is maintained being inserted into the body is 4 days and the second period calculated based on the capacity of the storage portion and the average daily dosage is 3 days, the second time point 430 may be set to be 3 days, which is a shorter period among the first period (4 days) and the second period (3 days).

Alternatively, when the first period during which safety is guaranteed when the cannula is maintained being inserted into the body is 3.5 days and the second period calculated based on the capacity of the storage portion and the average daily dosage is 4 days, the second time point 430 may be set to be 3.5 days, which is a shorter period among the first period (3.5 days) and the second period (4 days).

Meanwhile, when the material of the object maintained being inserted into the body of the user is changed, the capacity of the storage portion is changed, or the average daily dosage is changed, the controller may update the usable period of the drug infusion device in consideration of the change.

The controller may provide the impending expiration notification and the expiration notification via the drug infusion device. Alternatively, the controller may directly provide the impending expiration notification and the expiration notification. Alternatively, the controller may transmit data to a user terminal and the user terminal may provide the impending expiration notification and the expiration notification.

Figure 7:
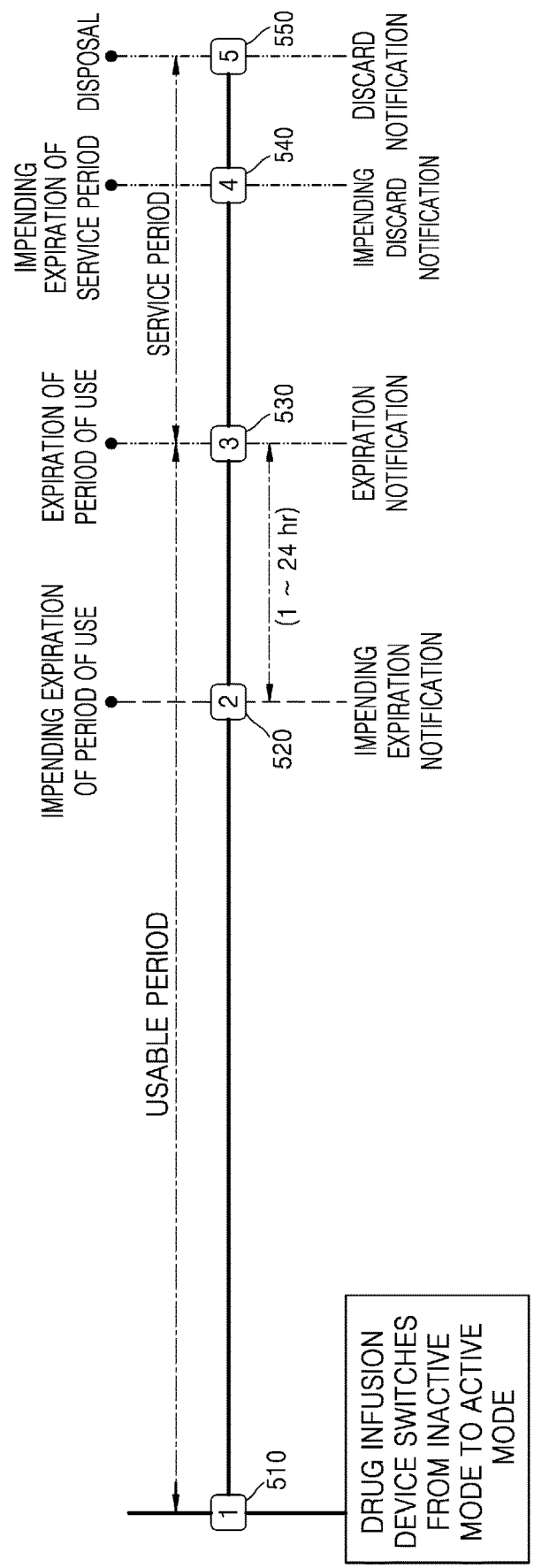
FIG. 7 is a diagram for describing an example of providing a notification according to a period of use of a drug infusion device, according to an embodiment.

FIG. 7 is a diagram for describing an example of providing a notification according to a period of use of a drug infusion device, according to an embodiment; and Referring to FIG. 7, a timeline to which a third time point 550 and a fourth time point 540 are further added in addition to a first time point 520 at which an impending expiration notification indicating that expiration of the period of use of the drug infusion device is imminent is provided and a second time point 530 at which an expiration notification indicating that the period of use of the drug infusion device has expired is provided is shown, compared to FIG. 6.

The drug infusion device may further include a service period in addition to a usable period. The drug infusion device may operate in an active mode for the usable period and the service period. In other words, the drug infusion device may operate normally when the service period has not passed, even when the usable period has passed.

The usable period may be a period known to a user through a manual or the like, whereas the service period may be a period not known to the user. The drug infusion device infuses drug to the user by operating normally in the active mode even in the service period such that the user may be infused with the drug from the drug infusion device for a certain period of time even when the usable period has expired.

A controller may provide an impending discard notification indicating that disposal the drug infusion device is imminent at the fourth time point 540 after a certain period from a use start time point 510, based on the usable period, the service period, and a user set time of the drug infusion device. The fourth time point 540 is a time point that is before the usable period and service period are elapsed from the use start time point 510.

In addition, the controller may provide a discard notification indicating that the drug infusion device is to be discarded, at the third time point 550 after the usable period and the service period from the use start time point 510. For example, the third time point 550 may be a time after 12 hours from the second time point 530.

According to an embodiment, the usable period and service period of the drug infusion device may be determined based on at least one of a material of an object maintained being inserted into a body of the user while the drug is infused to the user from the drug infusion device, a substance coated on the material, and a structure of the object.

When a cannula is maintained being inserted into the body of the user while the drug is infused into the user, the usable period and service period of the drug infusion device may be determined based on a material of the cannula. A period during which safety is guaranteed when the cannula is maintained being inserted into the body may vary depending on the material of the cannula, and thus the usable period and service period of the drug infusion device may be set differently depending on the material of the cannula.

For example, the material of the cannula may include Teflon, and in this case, the usable period and service period of the drug infusion device may be set to 4 days. At the third time point 550 after 4 days (96 hours) corresponding to the usable period and service period from the use start time point 510, the controller may provide the discard notification indicating that the drug infusion device needs to be discarded. Meanwhile, the usable period may be differently set when the material of the cannula includes another substance in addition to Teflon or includes a substance other than Teflon.

The user may receive the impending discard notification by setting an arbitrary time that is after a lapse of the usable period and before a lapse of the service period of the drug infusion device. For example, when the usable period and service period of the drug infusion device is set to 4 days (96 hours) and the user set time is 1 hour, the controller may provide the impending discard notification indicating that the disposal the drug infusion device is imminent at the fourth time point 540 after 95 hours (96 hours−1 hour) from the use start time point 510.

According to another embodiment, the usable period and service period of the drug infusion device may be determined based on capacity of a storage portion and an average daily dosage.

When the capacity of the storage portion is 240 units and the average daily dosage is 60 units, the usable period of the drug infusion device may be set to 4 days (240 units/60 units=4). In this case, the controller may provide the discard notification indicating that the drug infusion device needs to be discarded, at the third time point 550 after 4 days corresponding to the usable period and service period from the use start time point 510.

Also, the user may receive the impending discard notification by setting an arbitrary time that is after a lapse of the usable period and before a lapse of the service period the drug infusion device. For example, when the usable period and service period of the drug infusion device is set to 4 days (96 hours) and the user set time is 1 hour, the controller may provide the impending discard notification indicating that the disposal the drug infusion device is imminent at the fourth time point 540 after 95 hours (96 hours-1 hour) from the use start time point 510.

According to another embodiment, the usable period and service period of the drug infusion device may be determined based on the capacity of the storage portion, the average daily dosage, and at least one of the material of the object maintained being inserted into the body of the user while the drug is infused to the user from the drug infusion device, the substance coated on the material, and the structure of the object.

In detail, the controller may determine the usable period and service period of the drug infusion device by comparing a first period during which safety is guaranteed when the cannula is maintained being inserted into the body and a second period calculated based on the capacity of the storage portion and the average daily dosage.

For example, when the first period during which the safety is guaranteed when the cannula is maintained being inserted into the body is 4 days and the second period calculated based on the capacity of the storage portion and the average daily dosage is 3 days, the third time point 550 may be set to be 3 days, which is a shorter period among the first period (4 days) and the second period (3 days).

Alternatively, when the first period during which the safety is guaranteed when the cannula is maintained being inserted into the body is 3.5 days and the second period calculated based on the capacity of the storage portion and the average daily dosage is 4 days, the third time point 550 may be set to be 3.5 days, which is a shorter period among the first period (3.5 days) and the second period (4 days).

Meanwhile, the first time point 520 at which the expiration of the period of use of the drug infusion device is imminent and the second time point 530 at which the expiration notification indicating that the use of the drug infusion device has expired may be arbitrarily set. For example, when the third time point 550 is set to be after 4 days (96 hours) from the use start time point 510, the second time point 530 may be set to be after 3.5 days (84 hours) from the use start time point 510 and the first time point 520 may be set to be after 83 hours from the use start time point 510.

According to another embodiment, the usable period of the drug infusion device may be determined based on the capacity of storage portion and the average daily dosage, and a total period of the usable period and service period of the drug infusion device may be determined based on at least one of the material of the object maintained being inserted into the body of the user while the drug is infused to the user from the drug infusion device, the substance coated on the material, and the structure of the object.

In detail, the controller may determine the first period during which safety is guaranteed when the cannula is maintained being inserted into the body as the total period and determine the second period calculated based on the capacity of the storage portion and the average daily dosage as the usable period.

For example, when the first period during which safety is guaranteed when the cannula is maintained being inserted into the body is 4 days and the second period calculated based on the capacity of the storage portion and the average daily dosage is 3 days, the third time point 550 may be set to be 4 days that is the first period and the second time point 530 may be set to be 3 days that is the second period.

In other words, the present disclosure may provide convenience to the user via various types of notifications by providing the expiration notification to the user when the drug in the storage portion is depleted and providing the discard notification based on a safety guarantee period of the object inserted into the human body.

Methods of providing the impending expiration notification, the expiration notification, the impending discard notification, and the discard notification may be different from each other. A vibration period, vibration intensity, light-emitting diode (LED) color display, an LED blinking period, and a notification repeating period of the notifications may be different from each other. The user may easily determine to which one of the impending expiration notification, the expiration notification, the impending discard notification, and the discard notification a notification belongs only with how the corresponding notification is provided.

FIG. 8 is a flowchart of a method of providing a notification according to a period of use of a drug infusion device, according to an embodiment.

A controller may perform communication with the drug infusion device. The controller may be a component included in a user terminal, such as a smart phone or a PC, or may be a component independent from the user terminal. Alternatively, the controller may be a component included in the drug infusion device. Hereinafter, it is assumed that the drug infusion device and the controller perform communication by using a network.

In operation 610, the controller may determine a time point at which the drug infusion device switches from an inactive mode to an active mode as a use start time point.

The drug infusion device may switch from the inactive mode to the active mode via a predetermined operation. For example, the predetermined operation may be a drug replenishing operation. In detail, when drug is replenished in a storage portion, a plunger connected to a cover of the storage portion may move linearly such that one end portion of a connector member connected to the plunger contacts at least a part of a sensor unit. When the one end portion of the connector member contacts at least the part of the sensor unit, the drug infusion device may switch from the inactive mode to the active mode.

The drug infusion device may transmit an active mode switch signal to the controller. The controller may determine a time point at which the active mode switch signal is received from the drug infusion device as the use start time point.

In order for the controller to receive the active mode switch signal from the drug infusion device, a communication network needs to be formed between the controller and the drug infusion device.

The communication network between the controller and the drug infusion device may not be formed at a time point when the drug infusion device switches from the inactive mode to the active mode. In this case, the drug infusion device may transmit, to the controller, information about time elapsed after the switch to the active mode at the time point when the communication network is formed between the drug infusion device and the controller.

In operation 620, an impending expiration notification indicating that expiration of the period of use of the drug infusion device is imminent may be provided at a first time point after a certain period from the use start time point, based on a usable period and a user set time of the drug infusion device.

In operation 630, the controller may provide an expiration notification indicating that the period of use of the drug infusion device has expired at a second time point after the usable period from the use start time point.

According to an embodiment, the usable period of the drug infusion device may be determined based on a material of an object maintained being inserted into the body of the user while the drug is infused to the user from the drug infusion device. According to another embodiment, the usable period of the drug infusion device may be determined based on the capacity of a storage portion and an average daily dosage. According to another embodiment, the usable period of the drug infusion device may be determined based on the material of the object maintained being inserted into the body of the user while the drug is infused to the user from the drug infusion device, the capacity of the storage portion, and the average daily dosage.

The drug infusion device may further include a service period in addition to the usable period. The drug infusion device may operate in the active mode for the usable period and the service period. In other words, the drug infusion device may operate normally when the service period has not passed, even when the usable period has passed.

When the drug infusion device includes the service period in addition to the usable period, the controller may provide an impending discard notification indicating that disposal of the drug infusion device is imminent, at a fourth time point after a certain period from the use start time point, based on the usable period, service period, and user set time of the drug infusion device. The fourth time point is a time point that is before the usable period and service period are elapsed from the use start time point.

In addition, the controller may provide a discard notification indicating that the drug infusion device is to be discarded, at a third time point after the usable period and the service period from the use start time point.

According to an embodiment, the usable period and service period of the drug infusion device may be determined based on the material of the object maintained being inserted into the body of the user while the drug is infused to the user from the drug infusion device. According to another embodiment, the usable period and service period of the drug infusion device may be determined based on the capacity of the storage portion and the average daily dosage. According to another embodiment, the usable period of the drug infusion device may be determined based on the material of the object maintained being inserted into the body of the user while the drug is infused to the user from the drug infusion device, the capacity of the storage portion, and the average daily dosage.

When the drug infusion device further includes the service period in addition to the usable period, the first time point at which the expiration of the period of use of the drug infusion device is imminent and the second time point at which the expiration notification indicating that the use of drug infusion device has expired is provided may be arbitrarily set.

According to an embodiment of the present disclosure, convenience of use may be provided by determining a period of use of a drug infusion device based on the capacity of a storage portion of the drug infusion device and an average daily dosage, and providing a notification according to the period of use.

According to another embodiment of the present disclosure, a method of safely using a drug infusion device may be provided by determining a period of use of the drug infusion device based on a material of an object that is maintained being inserted into a users body while a drug is infused into the user from the drug infusion device.

Various embodiments of the present disclosure may be implemented as software (for example, a program) including one or more instructions stored in a machine-readable storage medium. For example, a processor of the machine may invoke and execute at least one of the one or more instructions stored from the storage medium. Accordingly, the machine is enabled to operate to perform at least one function according to the at least one invoked instruction. The one or more instructions may include code generated by a compiler or code executable by an interpreter. The machine-readable storage medium may be provided in the form of a non-transitory storage medium. Here, 'non-transitory' only means that the storage medium is a tangible device and does not contain a signal (for example, electromagnetic waves). This term does not distinguish a case where data is stored in the storage medium semi-permanently and a case where the data is stored in the storage medium temporarily.

According to an embodiment, a method according to various embodiments of the present disclosure may be provided by being included in a computer program product. The computer program product is a product that can be traded between sellers and buyers. The computer program product may be distributed in a form of machine-readable storage medium (for example, a compact disc read-only memory (CD-ROM)), or distributed through an application store (for example, Play Store™) or directly or online between two user devices (for example, download or upload). In the case of online distribution, at least a part of the computer program product may be temporarily stored or temporarily generated in the machine-readable storage medium such as a server of a manufacturer, a server of an application store, or a memory of a relay server.

Furthermore, in the specification, the term "unit" may be a hardware component such as a processor or circuit and/or a software component that is executed by a hardware component such as a processor.

The scope of the present disclosure is defined by the appended claims rather than the detailed description, and all changes or modifications within the scope of the appended claims and their equivalents will be construed as being included in the scope of the present disclosure.

What is claimed is:

1. A method of using a mobile drug infusion device, the method comprising:
    determining a time point at which the drug infusion device switches from an inactive mode to an active mode as a use start time point, wherein the drug infusion device includes a housing coupled to a skin of the user with a base body, a refillable insulin reservoir with a predetermined medication dosage sufficient for a predetermined dispensing period, a needle assembly, a storage portion, a driver, and a trigger member and wherein power is provided to at least one component in the active mode and removed in the inactive mode;
    providing an impending expiration notification indicating that expiration of the period of use of the drug infusion device is imminent at a first time point after a certain period from the use start time point, based on a usable period of the medication or the material in contact with the medication and a user set time of the drug infusion device; and
    providing an expiration notification indicating that the period of use of the drug infusion device has expired at a second time point after the usable period from the use start time point; and
    applying the drug infusion device to dispense insulin medication;
    wherein the method further comprises:
    (a) filling the drug infusion device with a first predetermined medication dosage sufficient for a first predetermined dispensing period, wherein the first predetermined dispensing period ends on a first repetitive day of a week selected for ease of remembrance by a user and attaching the device to user skin;
    (b) on the first repetitive day, removing from the user skin and refilling the device with a second predetermined medication dosage sufficient for a second predetermined dispensing period, wherein the second dispensing period ends on a second repetitive day of the week for ease of remembrance and attaching the device on the user for use until the second repetitive day; and
    (c) repeating steps a and b each week, wherein the device is refilled and installed on a repetitive twice-a-week replacement schedule on the first and second repetitive days of the week and wherein the first and second repetitive days of the week are programmed by the user into a remote controller that communicates with the device such that the user presets the first dispensing period to be no longer than 80 hours and the second dispensing period to be no longer than 90 hours, wherein the remote controller limits the first and second dispensing periods such that the first and second dispensing periods are not longer than the respective 80 and 90 hours.

2. The method of claim 1, further comprising providing a discard notification indicating that the drug infusion device is to be discarded at a third time point after a certain period from the second time point.

3. The method of claim 2, further comprising providing an impending discard notification indicating that disposal of the drug infusion device is imminent at a fourth time point between the second time point and the third time point.

4. The method of claim 3, wherein methods of providing the impending expiration notification, the expiration notification, the impending discard notification, and the discard notification are different from each other.

5. The method of claim 1, wherein
    the usable period is based on at least one of a material of an object that is maintained being inserted into a user's body while a drug is infused into the user from the drug infusion device, a substance coated on the material.

6. The method of claim 1, wherein the usable period is based on capacity of a storage portion of the drug infusion device and an average daily dosage.

7. An apparatus for providing a notification according to a period of use of a drug infusion device, the apparatus comprising:
    a memory storing at least one program; and
    a processor configured to perform an operation by executing the at least one program, the processor controlling the drug infusion device having a housing coupled to a skin of the user with a base body, a refillable insulin reservoir with a predetermined medication dosage sufficient for a predetermined dispensing period, a needle assembly, a storage portion, a driver, and a trigger member and wherein power is provided to at least one component in the active mode and removed in the inactive mode wherein the processor:
determines a time point at which the drug infusion device switches from an inactive mode to an active mode as a use start time point,
provides an impending expiration notification indicating that expiration of the period of use of the drug infusion device is imminent at a first time point after a certain period from the use start time point, based on a usable period of the medication or the material in contact with the medication and a user set time of the drug infusion device, and
provides an expiration notification indicating that the period of use of the drug infusion device has expired at a second time point after the usable period from the use start time point;

wherein the period of use comprises:
(a) filling the drug infusion device with a first predetermined medication dosage sufficient for a first predetermined dispensing period, wherein the first predetermined dispensing period ends on a first repetitive day of a week selected for ease of remembrance by a user and attaching the device to user skin;
(b) on the first repetitive day, removing from the user skin and refilling the device with a second predetermined medication dosage sufficient for a second predetermined dispensing period, wherein the second dispensing period ends on a second repetitive day of the week for ease of remembrance and attaching the device on the user for use until the second repetitive day; and
(c) repeating steps a and b each week, wherein the device is refilled and installed on a repetitive twice-a-week replacement schedule on the first and second repetitive days of the week and wherein the first and second repetitive days of the week are programmed by the user into a remote controller that communicates with the device such that the user presets the first dispensing period to be no longer than 80 hours and the second dispensing period to be no longer than 90 hours, wherein the remote controller limits the first and second dispensing periods such that the first and second dispensing periods are not longer than the respective 80 and 90 hours.

8. The apparatus of claim 7, wherein the processor provides a discard notification indicating that the drug infusion device is to be discarded at a third time point after a certain period from the second time point.

9. The apparatus of claim 7, wherein the processor provides an impending discard notification indicating that disposal of the drug infusion device is imminent at a fourth time point between the second time point and a third time point.

10. The apparatus of claim 7, wherein the usable period is based on at least one of a material of an object that is maintained being inserted into a user's body while a drug is infused into the user from the drug infusion device, a substance coated on the material.

11. The apparatus of claim 7, wherein the usable period is determined based on capacity of a storage portion of the drug infusion device and an average daily dosage.

12. The apparatus of claim 11, wherein an impending expiration notification, the expiration notification, the impending discard notification, and the discard notification are different from each other.

13. A computer program product comprising at least one computer-readable recording medium storing a program for:
determining a time point at which a drug infusion device switches from an inactive mode to an active mode as a use start time point, wherein the drug infusion device includes a housing coupled to a skin of the user with a base body, a refillable reservoir with a predetermined medication dosage sufficient for a predetermined dispensing period, a needle assembly, a storage portion, a driver, and a trigger member and wherein power is provided to at least one component in the active mode and removed in the inactive mode;
providing an impending replacement notification of the drug infusion device at a first time point after a certain period from the use start time point, based on a usable period of the medication or the material in contact with the medication and a user set time of the drug infusion device; and
providing an expiration notification indicating that a period of use of the drug infusion device has expired at a second point after the usable period from the use start time point;

wherein the period of use comprises:
(a) filling the drug infusion device with a first predetermined medication dosage sufficient for a first predetermined dispensing period, wherein the first predetermined dispensing period ends on a first repetitive day of a week selected for ease of remembrance by a user and attaching the device to user skin;
(b) on the first repetitive day, removing from the user skin and refilling the device with a second predetermined medication dosage sufficient for a second predetermined dispensing period, wherein the second dispensing period ends on a second repetitive day of the week for ease of remembrance and attaching the device on the user for use until the second repetitive day; and
(c) repeating steps a and b each week, wherein the device is refilled and installed on a repetitive twice-a-week replacement schedule on the first and second repetitive days of the week and wherein the first and second repetitive days of the week are programmed by the user into a remote controller that communicates with the device such that the user presets the first dispensing period to be no longer than 80 hours and the second dispensing period to be no longer than 90 hours, wherein the remote controller limits the first and second dispensing periods such that the first and second dispensing periods are not longer than the respective 80 and 90 hours.

14. The computer program product of claim 13, further comprising code to switch the drug infusion device from the inactive mode to the active mode, code to send the impending expiration notification, and code to send the expiration notification at the end of the useable period, wherein the impending expiration of period of use is between one to twenty four hours.

15. The computer program product of claim 13, further comprising a service period between a disposal and the useable period.

16. The computer program product of claim 13, further comprising code to code to send an impending discard notification and a discard notification.

* * * * *